US00PP08759P

United States Patent [19]

VandenBerg

[11] Patent Number: Plant 8,759

[45] Date of Patent: May 31, 1994

[54] CHRYSANTHEMUM PLANT NAMED YELLOW SANDY

[75] Inventor: Cornelis P. VandenBerg, Salinas, Calif.

[73] Assignee: Yoder Brothers, Inc., Barberton, Ohio

[21] Appl. No.: 983,135

[22] Filed: Nov. 30, 1992

[51] Int. Cl.[5] ..... A01H 5/00

[52] U.S. Cl. ..... Plt./82.2

[58] Field of Search ..... Plt. 82.2

[56] References Cited

U.S. PATENT DOCUMENTS

| | | | |
|---|---|---|---|
| PLT 5989 | 5/1987 | Duffett, et al. | PLT/82.2 |
| PLT 7531 | 5/1991 | Vanden Berg | PLT/82.2 |
| 4,616,099 | 10/1986 | Sparkes | 47/58 |

OTHER PUBLICATIONS

Broertjes et al., 1980, "A Mutant of a Mutant of a . . . Irradiation of Progression Radiation-Induced Mutants in a Mutation Breeding Programme with *C. morifolium*", Euphytica, 29:526–530.

Gosling, ed., 1979, "The Chrysanthemum Manual-6th edition", The National Chrysanthemum Society, London, Essex Telegraph Press, Ltd., pp. 329–336.

Broertjes, et al., 1978, "Application of Mutation Breeding Methods in the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and Rose Mutations Induced by X-Rays", Am. Soc. Hort. Sci. Proc., pp.613–620.

Broertjes, 1966, "Mutation Breeding of Chrysanthemums", Euphytica, 15:156–162.

Dowrick et al., 1966, "The Induction of Mutations in Chrysanthemum Using X- and Gamma Radiation", Euphytica, 15:204–210.

*Primary Examiner*—Howard J. Locker

*Attorney, Agent, or Firm*—Foley & Lardner

[57] ABSTRACT

A Chrysanthemum plant named Yellow Sandy particularly characterized by its flat capitulum form; daisy capitulum type; yellow ray floret color; diameter across face of capitulum of 63 to 73 mm when fully opened; branching pattern is spreading and prolific, with 7 to 9 breaks after pinch when grown outside under natural daylength in fall flowerings, and 5 to 7 breaks after pinch when grown in 10 cm pots for spring flowerings; natural season flower date of August 20 when planting rooted cuttings on June 25 in Salinas, Calif., and September 19 to October 4 when planting rooted cuttings June 15 in Hightstown, N.J.; flowering response of 45 to 49 days after rooting in no light/no shade programs in spring; plant height of 30 to 35 cm when grown in fall under natural daylength with no growth regulators, and 13 to 18 cm when grown in 10 cm pots in spring with 1 application of 2500 ppm B-9 SP; and durable, uniform performance.

1 Drawing Sheet

The present invention comprises a new and distinct cultivar of Chrysanthemum, botanically known as *Dendranthema grandiflora*, and referred to by the cultivar name Yellow Sandy.

Yellow Sandy, identified as 86-488B01, is a product of a mutation induction program. The new cultivar was discovered and selected by Cornelis P. VandenBerg on Nov. 13, 1989, in a controlled environment in Salinas, Calif. as one flowering plant within a flowering block established as rooted cuttings from stock plants which had been exposed as unrooted cuttings to an X-ray source of 1750 rads in Fort Myers, Fla. on May 25, 1989. The irradiated parent cultivar was the cultivar identified as Sandy, disclosed in U.S. Plant Pat. No. 7,531. Sandy is described as a flat daisy spray pot mum and garden mum with a soft honey-bronze ray floret color; diameter across face of capitulum of 63 to 73 mm when fully opened; spreading and prolific branching pattern, with 7 to 10 branches after pinch; average natural season flower date of August 20 to 28 in Salinas, Calif. and September 20 to October 1 in Hightstown, N.J.; photoperiodic flowering response to short days in photoperiodic controlled flowering programs of 45 to 49 days; and durable, uniform performance. The above description of Sandy has a wider range of values than disclosed in U.S. Plant Pat. No. 7,531 for Sandy, based on continued flower trials after the application for Sandy was filed.

The irradiation program resulting in Yellow Sandy had as its primary objective the expansion of color ranges of the parent cultivar Sandy. The irradiation program comprised irradiating cuttings of the parent cultivar at irradiation levels of 1500, 1750 and 2000 rads. A total of 1180 cuttings harvested from a total of 225 irradiated plants were planted on Sep. 11, Sep. 4 and Aug. 21, 1989, respectively. Of these 11 initial selections were made, which selections were then revegetated and reflowered. Four consecutive flowerings resulted in discarding 8 of the original 11 selections on Aug. 29, 1990. Three selections were maintained as PIs (Possible Introductions) and trialed for one year, ultimately resulting in discarding two of these three remaining selections on Sep. 23, 1991, and the decision to introduce the one remaining selection as Yellow Sandy.

The first act of asexual reproduction of Yellow Sandy was accomplished when vegetative cuttings were taken from the initial selection in December 1989 in a controlled environment in Salinas, Calif., by technicians working under supervision of Cornelis P. VandenBerg.

Horticultural examination of controlled flowerings of successive plantings has shown that the unique combination of characteristics as herein disclosed for Yellow Sandy are firmly fixed and are retained through successive generations of asexual reproduction.

Yellow Sandy has not been observed under all possible environmental conditions. The phenotype may vary significantly with variations in environment such as temperature, light intensity and daylength, without, however, any variance in genotype.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October. Spring flowerings were conducted in Salinas, Calif. under greenhouse conditions which approximate those generally used in commercial practice for small pot spring garden mum production.

The following traits have been repeatedly observed and are determined to be basic characteristics of Yellow Sandy, which, in combination, distinguish this Chrysanthemum as a new and distinct cultvar:

1. Flat capitulum form.
2. Daisy capitulum type.
3. Yellow ray floret color.
4. Diameter across face of capitulum of 63 to 73 mm when fully opened.
5. Branching pattern is spreading and prolific, with 7 to 9 breaks after pinch when grown outside under natural daylength in fall flowerings, and 5 to 7 breaks after pinch when grown in 10 cm pots for spring flowerings.
6. Natural season flower date of August 20 when planting rooted cuttings on June 25 in Salinas, Calif., and September 19 to October 4 when planting rooted cuttings June 15 in Hightstown, N.J.
7. Flowering response of 45 to 49 days after rooting in no light/no shade programs in spring.
8. Plant height of 30 to 35 cm when grown in fall under natural daylength with no growth regulators, and 13 to 18 cm when grown in 10 cm pots in spring with 1 application of 2500 ppm B-9 SP.
9. Durable, uniform performance.

The accompanying photographic drawing is a color photograph of Yellow Sandy Grown as a pinched garden mum under natural outside conditions in Salinas, Calif., with the colors being as nearly true as possible with illustrations of this type.

Of the commercial cultivars shown to the inventor, the most similar in comparison to Yellow Sandy is the parent cultivar Sandy. Most traits of Yellow Sandy are similar to those of Sandy, except for the ray floret color. The ray floret color of Yellow Sandy is yellow, while the ray floret color of Sandy is a soft honey-bronze. In addition, Yellow Sandy is 2 to 4 days slower in natural season flowerings when compared with Sandy.

In the following description color references are made to The Royal Horticultural Society Colour Chart. The color values were determined on plant material grown as a pinched garden mum grown under natural season outside conditions in Salinas, Calif. on Aug. 25, 1992.

CLASSIFICATION

*Botanical.*—*Dendranthema grandiflora* cv Yellow Sandy.

*Commercial.*—Flat daisy spray pot mum and garden mum.

INFLORESCENCE

A. Capitulum:
- *Form.*—Flat.
- *Type.*—Daisy.
- *Diameter across face.*—63 to 73 mm when fully opened.

B. Corolla of ray florets:
- *Color (general tonality from a distance of three meters).*—Yellow.
- *Color (upper surface).*—5A.
- *Color (under surface).*—5A.
- *Shape.*—Flat, straight, oblong.

C. Corolla of disc florets:
- *Color (mature).*—14A.
- *Color (immature).*—Closest to 14B, slightly tinged with 151A.

D. Reproductive organs:
- *Androecium.*—Present on disc florets only; moderate pollen.
- *Gynoecium.*—Present on both ray and disc florets.

PLANT

A. General appearance:
- *Height.*—30 to 35 cm when grown in fall under natural daylength with no growth regulators, and 13 to 18 cm when grown in 10 cm pots in spring with 1 application of 2500 ppm B-9 SP.
- *Branching pattern.*—Spreading and prolific, with 7 to 9 breaks after pinch when grown outside under natural daylength in fall flowerings, and 5 to 7 breaks after pinch when grown in 10 cm pots for spring flowerings.

B. Foliage:
- *Color (upper surface).*—147A.
- *Color (under surface).*—147B.
- *Shape.*—See photograph.

I claim:

1. A new and distinct Chrysanthemum plant named Yellow Sandy, as described and illustrated.

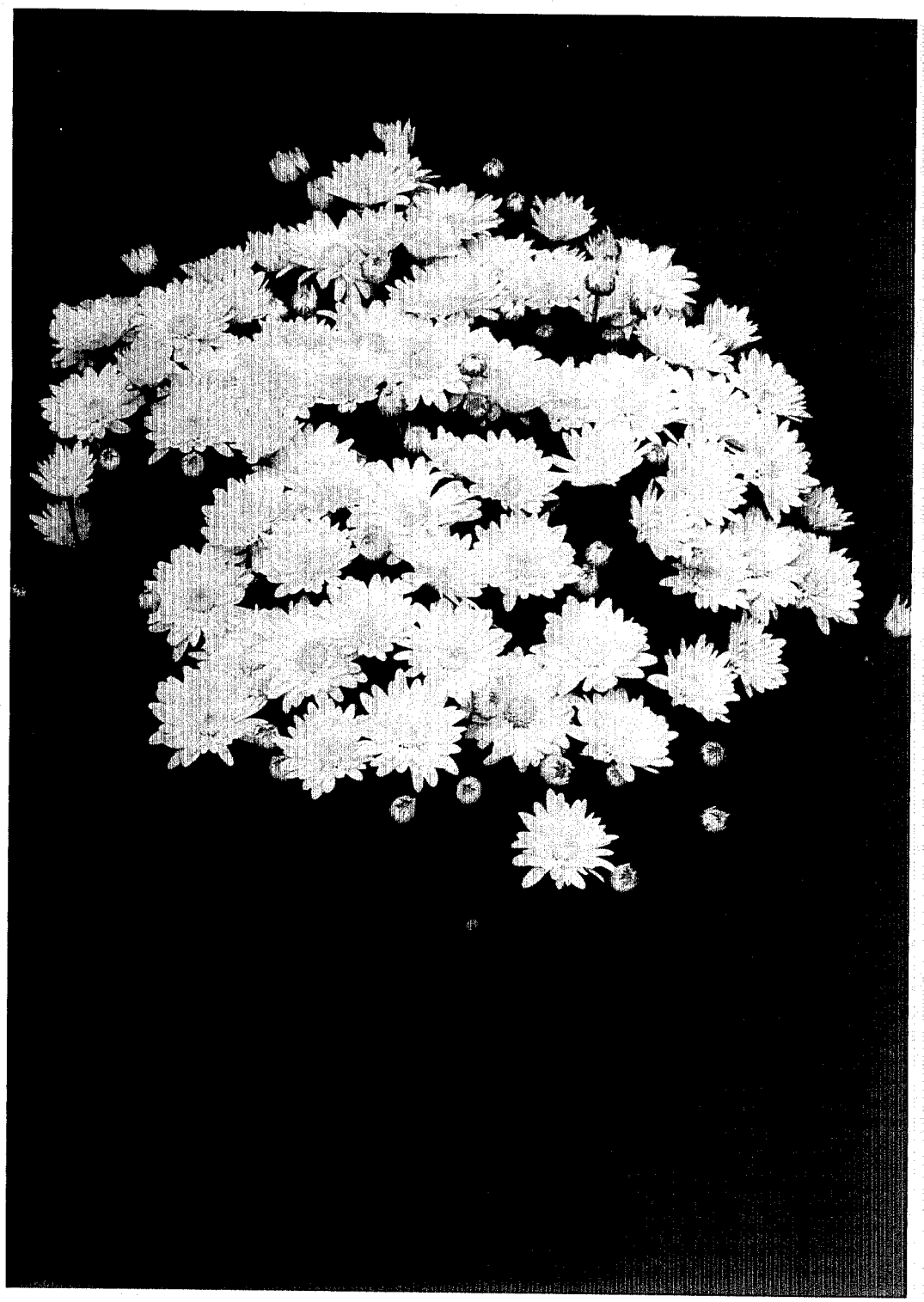

* * * * *